United States Patent
Arumugam et al.

(10) Patent No.: US 6,527,690 B2
(45) Date of Patent: Mar. 4, 2003

(54) PURIFICATION OF PHENYL ESTER SALTS

(76) Inventors: Bhaskar Krishna Arumugam, 3909 Lake Valley Ct., Kingsport, TN (US) 37664; Michael Eugene Burns, 7132 Valley Falls Ct., Hamilton, OH (US) 45011; Dimmick Lee Bymaster, 139 Gordon La., Batesville, AR (US) 72501; Jeffrey Scott DuPont, 1012 Seibel La., Cincinnati, OH (US) 45238; Robert Richard Dykstra, 7715 Mitchell Park Dr., Cleves, OH (US) 45002; Robert Lee Eagan, 4107 Grey Fox Dr., Kingsport, TN (US) 37664; Eddie Joseph Eckart, 65 Whippoorwill Rd., Batesville, AR (US) 72501; Jarvey Eugene Felty, Jr., 706 Ford Creek Rd., Gray, TN (US) 37615; Kevin John Fontenot, 1021 Timberidge Trail, Kingsport, TN (US) 37660; Jeffrey William Green, 3335 Juniper, Batesville, AR (US) 72501; Shane Kipley Kirk, 331 Dogwood St., Church Hill, TN (US) 37642; Gary Paul Lutz, 3801 Chase Wellseley 222, Richmond, VA (US) 23233; Tony Lee Sander, 3808 Woodmont Park La., Louisville, KY (US) 40245; Thomas Hugh Williams, P.O. Box 67, Fall Branch, TN (US) 37656; George Chester Zima, 1000 University Blvd. F45, Kingsport, TN (US) 37660

( * ) Notice: Subject to any disclaimer, the term of this patent is extended or adjusted under 35 U.S.C. 154(b) by 0 days.

(21) Appl. No.: 09/871,695

(22) Filed: Jun. 4, 2001

(65) Prior Publication Data

US 2002/0128505 A1 Sep. 12, 2002

Related U.S. Application Data

(60) Provisional application No. 60/208,498, filed on Jun. 2, 2000.

(51) Int. Cl.[7] .............................................. C07C 231/00
(52) U.S. Cl. ........................... 584/70; 584/68; 560/141; 560/142
(58) Field of Search ........................... 554/70; 560/141, 560/142; 584/36, 68

(56) References Cited

U.S. PATENT DOCUMENTS

| 2,768,222 A | 10/1956 | Nixon et al. |
| 4,107,443 A | 8/1978 | Mark et al. |

(List continued on next page.)

FOREIGN PATENT DOCUMENTS

| EP | 0 402 339 A1 | 12/1990 |
| EP | 0 415 472 A1 | 3/1991 |

(List continued on next page.)

OTHER PUBLICATIONS

Hansen, et al, "Solubility Parameters", Encyclopedia of Chemical Technology, Second Edition, Supplemental vol., Wiley—Interscience Publication, 11 97 1 and Hansen Solubility Parameters—A User's Handbook, C. M. Hansen, CRC Press, Washington, D.C., 2000, pp. 889–910.

Primary Examiner—Deborah D. Carr

(57) ABSTRACT

The invention relates to a process for purifying and decolorizing a phenyl ester salt. The process combines a phenyl ester salt with a solvent to form a mixture and then stirs the mixture to form a slurry. The phenyl ester salt is substantially insoluble in this solvent. The process then collects the phenyl ester salt from the slurry. The collected phenyl ester salt may then be optionally dried or recrystallized. The collected phenyl ester salt is dissolved in a solvent to form a solution. The solution is decolorized and then spray dried to form a powder of the phenyl ester salt. As a result of the process the phenyl ester salt powder has a higher purity and an improved color as compared to the starting phenyl ester salt.

13 Claims, 4 Drawing Sheets

U.S. PATENT DOCUMENTS

| | | |
|---|---|---|
| 4,424,138 A | 1/1984 | Candlin et al. |
| 4,457,858 A | 7/1984 | Saran et al. |
| 4,460,700 A | 7/1984 | Candlin et al. |
| 4,468,476 A | 8/1984 | Yang et al. |
| 4,629,771 A | 12/1986 | Candlin et al. |
| 4,634,551 A | 1/1987 | Burns et al. |
| 4,681,695 A | 7/1987 | Divo |
| 4,852,989 A | 8/1989 | Burns et al. |
| 5,298,611 A | 3/1994 | Navia et al. |
| 5,391,780 A | 2/1995 | Zima et al. |
| 5,391,783 A | 2/1995 | Colignon et al. |
| 5,393,901 A | 2/1995 | Zima et al. |
| 5,393,905 A | 2/1995 | Zima et al. |
| 5,414,099 A | 5/1995 | Heinzman et al. |
| 5,429,773 A | 7/1995 | Sherry et al. |
| 5,466,840 A * | 11/1995 | Lutz et al. .................. 554/70 |
| 5,523,434 A | 6/1996 | Burns et al. |
| 5,534,195 A | 7/1996 | Chapman et al. |
| 5,534,196 A | 7/1996 | Chapman et al. |
| 5,650,527 A | 7/1997 | Lutz et al. |
| 5,717,118 A | 2/1998 | Lutz et al. |

FOREIGN PATENT DOCUMENTS

| | | |
|---|---|---|
| EP | 0 484 634 A1 | 5/1992 |
| GB | 2249104 | 4/1992 |
| JP | 6-176648 | 6/1994 |
| JP | 6-306042 | 11/1994 |
| JP | 07 228566 | 8/1995 |
| JP | 8-245549 | 9/1996 |
| JP | 9-110824 | 4/1997 |
| WO | WO 89/08718 | 9/1989 |
| WO | WO 94/18159 | 8/1994 |
| WO | WO 94/28104 | 12/1994 |
| WO | WO 94/28106 | 12/1994 |
| WO | WO 95/07883 | 3/1995 |
| WO | WO 96/16148 | 5/1996 |
| WO | WO 97/27280 | 7/1997 |
| WO | WO 99/09004 | 2/1999 |

* cited by examiner

PURIFICATION OF PHENYL ESTER SALTS

This application claims priority under 35 U.S.C. § 119 to provisional application Ser. No. 60/208,498, filed Jun. 2, 2000, which is incorporated herein by reference.

FIELD OF THE INVENTION

The invention relates to a process for purifying and decolorizing a phenyl ester salt. Phenyl ester salts are used as bleach activators in laundry detergents and other cleaning formulations.

BACKGROUND OF THE INVENTION

Sodium hypochlorite and hydrogen peroxide are well known for their bleaching properties. As a bleaching agent in laundry detergents, hydrogen peroxide has the advantage of being safe to use with many fabric dyes. However, hydrogen peroxide bleaches are not effective at temperatures below 50° C. This limits their use as most laundering is carried out at temperatures below about 40° C. For this reason, various peroxyacids were developed as alternative bleaching agents for use in laundry detergents. The peroxyacids were generally found to be effective bleaching agents at the lower laundering temperatures. Because of their chemical instability and potential safety hazards, however, peroxyacids themselves are generally unsuitable for storage and handling.

Bleach activators were developed to address storage and handling concerns associated with peroxyacids. Bleach activators have the ability to hydrolyze under laundering conditions, effectively producing peroxyacids, even at lower temperatures, e.g. below 40° C. Bleach activators have the further advantage of being stable when stored in solid form at room temperature. These properties permit the use of bleach activators in a variety of laundry detergents and other cleaning formulations.

An important class of bleach activators is phenyl ester salts. Formulas (I) and (II), below, depict the generic chemical formula of phenyl ester salts typically used as bleach activators:

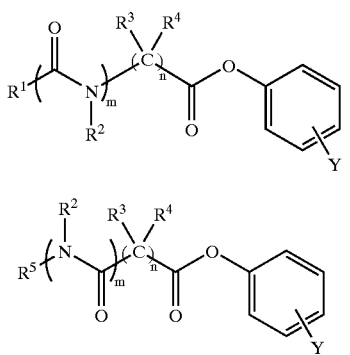

The various substituents and variables of the phenyl ester salts of formulas (I) and (II) are discussed below in the Detailed Description.

To be useful as a bleach activator, a phenyl ester salt must meet certain fitness-for-use parameters. The phenyl ester salt should have an acceptable perhydrolysis rate, that is the rate at which it reacts with bleach to form the corresponding peroxyacid. Perhydrolysis rate is a measure of the percentage of the phenyl ester salt that produces peroxyacid in a certain amount of time at a certain temperature. The peroxyacid must be produced quickly enough to be useful during the length of time and at the temperature of a typical wash cycle.

While it is important that phenyl ester salts employed in consumer detergent formulations have a high perhydrolysis rate, phenyl ester salts should also have acceptable levels of color and/or assay (or purity). These fitness-for-use parameters are also important and do not necessarily equate with a high perhydrolysis rate. A further problem is that the processes known in the art for making phenyl ester salts often produce products of highly variable quality requiring extensive purification or isolation procedures. Accordingly there exists a need for a process which purifies and decolorizes a phenyl ester salt to satisfy the fitness-for-use parameters of color, assay, and perhydrolysis rate.

SUMMARY OF THE INVENTION

The invention is a process for purifying and decolorizing a phenyl ester salt. The process combining a phenyl ester salt with a solvent to form a mixture. The phenyl ester salt is substantially insoluble in the solvent. The mixture is then stirred for a time sufficient to form a slurry. The phenyl ester salt is collected from the slurry and may then be dried. Drying the collected phenyl ester salt is an optional step. As another optional step, the collected phenyl ester salt may be recrystallized. The collected phenyl ester salt is then dissolved in a solvent to form a solution. The phenyl ester salt solution is decolorized and then spray dried to form a powder of the phenyl ester salt. As a result of the process, the phenyl ester salt powder has a higher purity and an improved color as compared to the starting phenyl ester salt. While each process step may be performed independently of the others, performing individual steps results in, at best, modest improvements in purity (or assay) and color. Practicing the process of the invention achieves the maximum benefits in purity and color and may also improve the phenyl ester salt's perhydrolysis rate.

DETAILED DESCRIPTION

Figure 1:
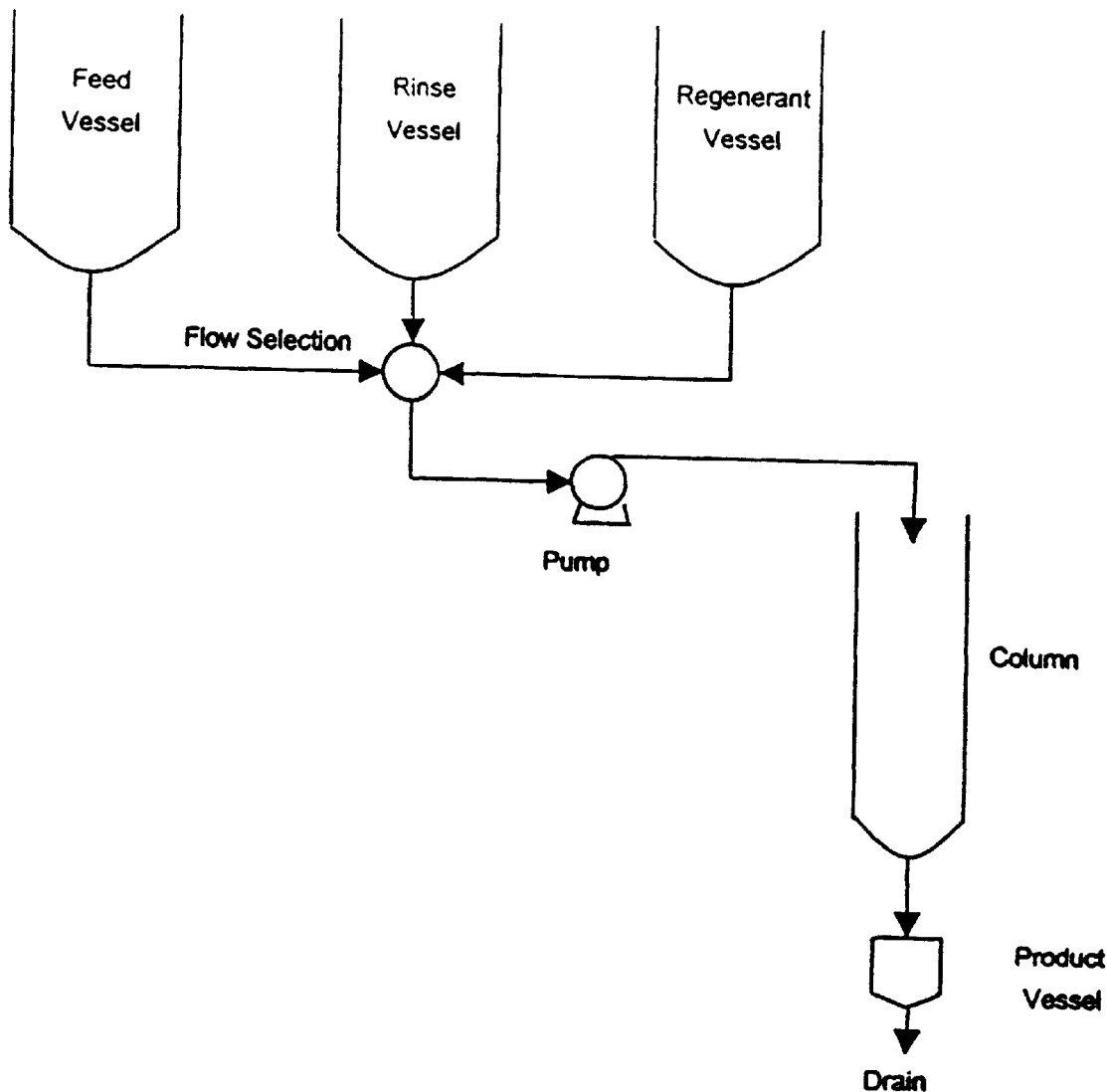
FIG. 1 is a schematic of the column test apparatus used to evaluate decolorization resins.

The invention is a process for purifying and decolorizing a phenyl ester salt. The process combining a phenyl ester salt with a solvent to form a mixture. The phenyl ester salt is substantially insoluble in the solvent. The mixture is then stirred for a time sufficient to form a slurry. The phenyl ester salt is collected from the slurry and may then be dried. Drying the collected phenyl ester salt is an optional step. As another optional step, the collected phenyl ester salt may be recrystallized. The collected phenyl ester salt is then dissolved in a solvent to form a solution. The phenyl ester salt solution is decolorized and then spray dried to form a powder of the phenyl ester salt. As a result of the process, the phenyl ester salt powder has a higher purity and an improved color as compared to the starting phenyl ester salt. While each process step may be performed independently of the others, performing individual steps results in, at best, modest improvements in purity (or assay) and color. Practicing the process of the invention achieves the maximum benefits in purity and color. A further advantageous result of the process is an improved perhydrolysis rate for the purified and decolorized phenyl ester salt. Each step of the process is described in more detail below.

Phenyl Ester Salts

Phenyl ester salts are used as bleach activators. As bleach activators, the phenyl ester salts should have good color and good assay. An effective bleach activator, phenyl ester salts readily react with bleach to form the corresponding peroxyacid. Exemplary phenyl ester salts, which are used as bleach activators, are described in U.S. Pat. Nos. 4,634,551; 4,852,989; 5,391,780; 5,393,905; 5,393,901; 5,414,099; 5,466,840; 5,523,434; 5,650,527; and 5,717,118; as well as in published PCT applications WO 94/18159, WO 95/07883, WO 96/16148, and WO 99/09004. These U.S. patents and published PCT applications are incorporated herein in their entirety.

Generally, phenyl ester salts are compounds of formula (I) or (II):

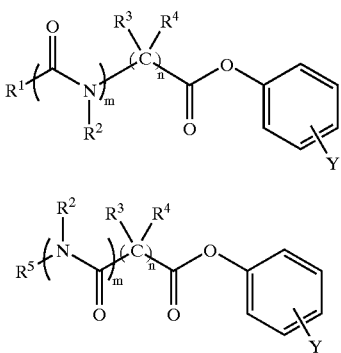

In formula (I) or (II), $R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Preferably, $R^1$ is selected from $C_6$–$C_{10}$ alkyl, and $C_6$–$C_{10}$ aryl.

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Alternatively, in formula II, $R^2$ and $R^5$, together with the nitrogen carrying them, form a $C_3$–$C_{10}$ heterocycle. This heterocycle may or may not contain additional heteroatoms selected from the group consisting of: nitrogen, oxygen, sulfur, or phosphorous. Preferably, $R^2$ is hydrogen, and $R^5$ is selected from hydrogen, $C_6$–$C_{10}$ alkyl, and $C_6$–$C_{10}$ aryl.

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl. The $R^3$ and $R^4$ groups, together with the carbon carrying them, may form a $C_3$–$C_{10}$ cycloalkyl group. This cycloalkyl group may or may not contain heteroatoms selected from the group consisting of: nitrogen, oxygen, sulfur, or phosphorous. Preferably, $R^3$ and $R^4$ are independently selected in each instance from hydrogen and methyl.

The substituent Y on the phenyl ring is selected from $SO_3^-M^+$, $CO_2^-M^+$, $SO_4^-M^+$, and $N^+(R^7)_3X^-$. M represents a cation, and may be selected from hydrogen, ammonium and alkali metal atom. $R^7$ in each instance is independently a $C_1$–$C_4$ alkyl group. X is an anion, and may be selected from a halide, hydroxide, methylsulfate, or acetate ion. Preferably, Y is selected from $SO_3^-M^+$, and $CO_2^-M^+$; where M is a sodium ion.

The phenyl ring may also be further substituted with 1 to 4 other substituents. The substituents may be electron-withdrawing or electron-donating groups. The substituents may, for example, be chosen to adjust the perhydrolysis rate, to adjust the hydrophilic/hydrophobic nature of the phenyl ester salt, or to adjust the solubility of the phenyl ester salt. Possible groups include, but are not limited to, hydroxyl, halogen, $C_1$–$C_{10}$ alkyl, $C_2$–$C_{10}$ alkenyl, $C_2$–$C_{10}$ alkynyl, $C_3$–$C_{10}$ cycloalkyl, and $C_1$–$C_{10}$ alkoxy, and amino groups. When the phenyl ester salts are to be used as bleach activators, it is also desirable to have electron-withdrawing groups on the phenyl ring, to facilitate perhydrolysis or bleach activation.

The value of "m" is 0 or 1 and represents the presence or absence of an amido group in the compound. Acceptable values for "n" may range from about 0 to 20, and preferred values for "n" include from about 0 to about 6.

A particularly preferred phenyl ester salt is sodium nonanamidohexanoyloxybenzenesulfonate, a phenyl ester salt of formula (I). Sodium nonanamidohexanoyloxybenzenesulfonate is discussed below as an example of the phenyl ester salts which may be purified and decolorized using the process of the invention. In the following discussion, sodium nonanamidohexanoyloxybenzenesulfonate is referred to as "Compound (1)." As discussed above, phenyl ester salts can be prepared in various ways. For example, sodium nonanamidohexanoyloxybenzenesulfonate, Compound (1), can be prepared by reacting a $C_9$ fatty acid with caprolactam to form 6-nonanoylamidohexanoic acid. Sodium p-hydroxybenzenesulfonate and acetic anhydride is then reacted with the 6-nonanoylamidohexanoic acid in a solvent to form Compound (1), sodium nonanamidohexanoyloxybenzenesulfonate. This reaction scheme is shown below in Scheme 1:

Equation 1A

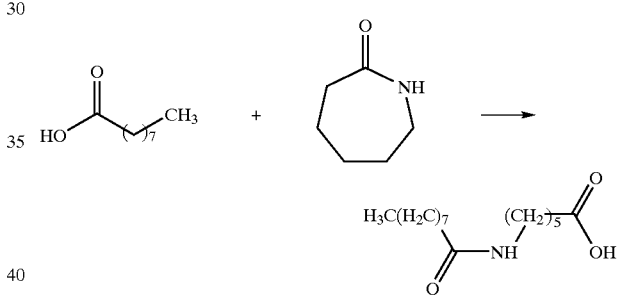

Equation 1B

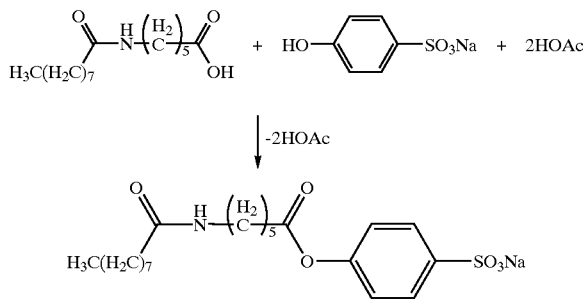

The process of the invention can be used to improve the purity and color of any phenyl ester salt. The starting phenyl ester salt may be from a reaction product mixture with the reaction solvent (or a portion thereof) removed. Typical reaction product mixtures contain the phenyl ester salt and residual reaction solvent, e.g. sulfolane or other polar aprotic solvents. Or, the starting phenyl ester salt may be the product after drying. Alternatively, the starting phenyl ester salt may have been previously worked up to remove unwanted impurities, reaction by-products, solvent, color bodies, etc.

Preferably, the phenyl ester salt material contains less than about 10 wt % residual solvent, more preferably less than about 5 wt %. Volatile organic compounds, such as solvents or acetic acid used in the synthesis and purification of phenyl ester salts, may be removed by evaporation or other drying techniques known in the art. When a volatile organic such as acetic acid is present, it is preferable to remove it by evaporation. More generally speaking, the starting phenyl ester salt may be any phenyl ester salt that does not meet its desired purity (also known as assay) and/or color. The process of the invention may also, advantageously, improve the perhydrolysis rate of the phenyl ester salt.

(A) Forming a Phenyl Ester Salt/Solvent Mixture

As a first step, the process of the invention combines a phenyl ester salt with a solvent to form a mixture. The phenyl ester salt is substantially insoluble in the solvent and preferably is completely insoluble in the solvent. While the phenyl ester salt is substantially insoluble in the solvent, the impurities, including color bodies, within the starting phenyl ester salt material should dissolve in the solvent. Lacking substantial solubility in the solvent allows the phenyl ester salt to be separated from the impurities without minimal loss of the phenyl ester salt due to solubility in the solvent. The solvent should also preferably be capable of easy removal (e.g. have a low boiling point) to allow easy removal from the phenyl ester salt. It is also preferred that the solvent be relatively inexpensive, non-hazardous, and non-toxic. Exemplary solvents which may be used in the process of the invention include, but are not limited to, methanol, ethanol, 1-propanol, 2-propanol, cyclohexanol, acetone, methyl ethyl ketone, acetonitrile, diethoxymethane, and acetic acid, as well as mixtures of those solvents and aqueous mixtures of these solvents.

The phenyl ester salt and the solvent may be combined in any amounts that permit the resulting mixture to be stirred such that a slurry of the phenyl ester salt and solvent may be formed. The mixture typically comprises about 5–80 weight percent of the phenyl ester salt and 20–95 weight percent solvent based on the total weight of the mixture. A particularly preferred mixture contains about 30–60 weight percent of the phenyl ester salt and 40–70 weight percent solvent. More solvent may be added as needed to achieve good stirring.

(B) Stirring the Mixture to Form a Slurry

Once the phenyl ester salt and the solvent are combined to form a mixture, the mixture is stirred to form a slurry of the phenyl ester salt in the solvent. The mixture may stirred or otherwise agitated by any means known in the art to form a slurry.

Slurrying (or "washing") a phenyl ester salt according to the invention removes color bodies and other impurities from the phenyl ester salt. It is preferred that the slurry be stirred for a period of time. Typically, the amount of time will vary depending on the amount of phenyl ester salt and the scale of the process. In general, the amount of time may range from about 0.5 hours to 24 hours. Preferably, the amount of time ranges from 0.5 to 12 hours, and more preferably is about 1 to 4 hours.

As discussed, the first two steps of a process of the invention, combine and then slurry a phenyl ester salt with a solvent. These steps generally are performed at ambient temperature. Lower temperatures will minimize the amount of the solid phenyl ester salt that may dissolve in the solvent, thus decrease the amount of the phenyl ester salt lost to dissolution. There may be situations where it is necessary or advantageous to heat the phenyl ester salt and solvent mixture. For example, some amount of heating may be desirable to more efficiently stir the mixture to form a slurry. The solvent may be preheated or cooled before mixing with the phenyl ester salt.

(C) Collecting the Phenyl Ester Salt from the Slurry

After the mixture is stirred to form a slurry, the phenyl ester salt is collected from the slurry. The phenyl ester salt may be collected by any solid/liquid separation technique known in the art. Such techniques include, for example, filtering the slurry, centrifuging the slurry, or decanting the solvent from the slurry. Collecting the phenyl ester salt can be carried out on any device capable efficiently separating solid and liquid phases (e.g., vacuum filtration or centrifugation).

In a preferred embodiment, steps (a)–(c) of the process of the invention are repeated using the collected phenyl ester salt. In other words, after collection step, the collected phenyl ester salt is again combined with a solvent to form a mixture, which is then stirred to form a slurry as described above. The process may be repeated using the same or a different solvent. Preferably, the process is repeated two to three times.

For large scale applications, batch, semi-batch, and continuous mixing and slurrying may be appropriate. A batch process is one where the phenyl ester salt and the solvent are added to the vessel as a lot and the resulting mixture stirred to form a slurry followed by removing the slurry to collect the phenyl ester salt. A semibatch process (sometimes referred to as semicontinuous) involves the feeding of additional solvent and phenyl ester salt during the formation of slurry and/or the removal of slurry from the mixer. A continuous process utilizes a continuous feed of the phenyl ester salt and solvent, stirring to form the slurry, and a continuous removal of the product slurry. While batch and semibatch processes are normally performed in a single vessel, continuous processes can require multiple agitated vessels in series. The larger the desired capacity of the process the more likely the process will be a continuous one since the operating cost of batch processes are normally much higher than continuous processes. However, there are times when the perhydrolysis rate of a phenyl ester salt can be more readily achieved in a batch process, but is not conveniently achieved in a continuous process. The semi-batch process is a technique used to maximize output of a plant that would otherwise be batch.

(D) Optionally Drying the Collected Phenyl Ester Salt

After the collecting the phenyl ester salt from the slurry, the phenyl ester salt may be dried to remove solvent left over from the mixture. Drying may be required if the solvent later interferes with the efficiency of the media used for color removal or is not a suitable solvent for spray drying. The phenyl ester salt may be dried in air, by heating, by vacuum, or with other drying techniques or combinations of drying techniques known in the art. Preferably, the phenyl ester salt is heated to a temperature at which there is no substantial decomposition of the phenyl ester salt. Drying temperatures of less than about 150° C. are generally preferred. Higher temperatures may be used to remove higher boiling solvents. At higher temperatures, the drying time may be reduced to avoid product decomposition. Or, the phenyl ester salt may preferably be dried first on the filter from the collection step and then under reduced pressure at about 110° C. Suitable drying devices include: ring dryer, tray dryer, rotary-cone vacuum dryer.

(E) Optionally Recrystallizing the Collected Phenyl Ester Salt

The process of the invention for purifying and decolorizing a phenyl ester salt may also include a step of recrystallizing the phenyl ester salt collected from the slurry. The collected phenyl ester salt may have been dried as discussed above or may be recrystallized directly after collection from the slurry. In some instances, where a high boiling solvent such as sulfolane was the reaction solvent, residual solvent may present in the phenyl ester salt material collected from the slurry. Typically recrystallization involves three steps. In the first step, the collected phenyl ester is dissolved in a solvent. The solvent may be heated to a temperature where the phenyl ester salt dissolves in the solvent. Exemplary solvents suitable for dissolving the phenyl ester salt include acetic acid and methanol-water mixtures. As with any other solution in the process, this solution may be filtered, centrifuged, etc. to remove any insoluble material.

In the second recrystallization step, the cooling step, heat or solvent is be removed from the system in order to initiate crystallization. Heat can be removed either through the use of a heat exchanger (i.e., cooling coils or jacket) or through adiabatic cooling, which involves lowering the internal pressure of the system resulting in evaporative cooling. Adiabatic cooling can be carried out by either condensing the evaporated solvent (i.e., distillate) and returning the solvent back to the crystallization unit, or by collecting the distillate in a separate receiver. The former method does not result in a change in solvent concentration whereas the latter method does. The preferred method is to carry out the adiabatic cooling with return of the distillate such that the concentration remains essentially unchanged. When using acetic acid as the recrystallization solvent, adiabatic cooling of the solution is the preferred method. Optimal crystal growth is realized from adiabatic cooling. Furthermore, adiabatic cooling generally results in larger crystals, which can easily be separated from recrystallization solvent (dissolution liquors) via filtration. When batches are cooled using cooling coils, sometimes more than 50% of the batches experience filtration problems (i.e., slow filtration, "mud" batches, etc.). This results in poor separation from the dissolution liquors, which consequently causes the need to reprocess (rework) the material in order to achieve the desired quality.

Alternative methods can also be employed as a means for improving the crystallization process. For example, a crystalline form of the phenyl ester salt can be used to seed the batch at a temperature just above the nucleation temperature. It is expected that similar results can be achieved during the crystallization process without seeding. However, seeding may be appropriate to catalyze the crystallization process. Other alternative methods to improve the crystallization process that are known to those skilled in the art may also be employed.

Phenyl ester salts may also be recrystallized from aqueous solutions. At first glance, the use of water (or an alcohol) as a solvent to replace acetic acid typically used for the purification of crude phenyl ester salts is not an obvious choice. Japanese Patent No. 6-306,042 (1995), for example, reports that compounds related to phenyl ester salts in water or alcohol are subject to hydrolysis or solvolysis at elevated temperatures. Indeed, initial work on water crystallization confirmed that phenyl ester salts, such as Compound (1), did undergo hydrolysis at elevated temperatures. Typical losses of Compound (1) were in the range of 5–7.5% at 90° C. Further studies indicated that operating at a pH range of 4–6 minimizes the hydrolysis of Compound (1) at 90° C. to about 2.2%.

The following is a preferred process for purifying phenyl ester salts via water crystallization: A slurry of crude Compound (1) in deionized water was adjusted to pH of about 5 with sulfuric acid and heated to 85° C. over 30 minutes to form a solution. Once the crude Compound (1) was in solution, the mixture was agitated at a pot temperature of 80–85° C. for 1 hour. The solution was cooled to 25° C. over a 3.5 to 8 hour period to affect crystallization of Compound (1). Crystallized Compound (1) was drained from the unit as a slurry in water, and a portion of this material was centrifuged. The centrate was decanted, and an equal amount of deionized water was added as a wash and the contents were reslurried for 1–3 minutes. Centrifugation conditions were repeated a second time, with an equal amount of deionized water added as a wash for another reslurry. Again, centrifugation conditions were repeated, and the wet cake was recovered and dried in a vacuum oven with a nitrogen purge at 70° C. This affords a phenyl ester salt, such as Compound (1), as a white crystalline solid in high yield (typically greater than 80% recovery). The phenyl ester salt is also recovered in high purity with an HPLC assay in the range of 95–100%, and with a color measured as Hunter color L value in the range of 85–95.

Recrystallizing phenyl ester salts using water crystallization may also be improved by adding a co-solvent. The co-solvent is preferably added after crystallization (or nucleation) of the phenyl ester salt has begun. The use of a co-solvent can reduce the surface tension of the foam and enhance the dissolution of water insoluble species. Adding a co-solvent can also speed the isolation of the recrystallized phenyl ester salt and thus eliminate the need for any special isolation equipment. The co-solvent may be any solvent that aids in solvating the phenyl ester salt or other species present in the phenyl ester salt material to be recrystallized. The co-solvent should not have a significant adverse impact on the recrystallization of the phenyl ester salt. By reducing the surface tension, the co-solvent may also aid in filtering the slurry of recrystallized phenyl ester salt form the aqueous recrystallization liquor. A mixture of co-solvents may also be used. The co-solvent(s) may be chosen for their specific solvating properties.

One method to classify solvents is by the Hansen solubility parameters. Hansen, C. M.; Beerbower, A.. "Solubility Parameters", Encyclopedia of Chemical Technology, Second Edition. Supplemental Volume, Wiley-Interscience Publication, 11 97 1 and "Hansen Solubility Parameters—A User's Handbook", C. M. Hansen, CRC Press, Washington, D.C., 2000. There are four types of Hansen solubility parameters: total, polar, nonpolar, and hydrogen bonding. Hansen Polar and hydrogen bonding solubility parameters are routinely used as an efficient means in classifying and selecting a range of solvents that are effective at solvating a particular molecule. Solvents evaluated as potential co-solvents have Hansen polar solubility parameters in the range 4.1 to 12.3 and Hansen hydrogen bonding parameters in the range o f 6.1 to 22.3. This allows the solubility parameters of the mother liquor (water plus co-solvent) to shift from the extreme values found with water (16.0 and 42.3) to values that provide enhanced solubilities for impurities in the phenyl ester salt material being recrystallized. Furthermore, adding such a co-solvent only slightly increases the solubility of the phenyl ester salt while retaining the benefits of water-based recrystallization (easier hydrolysis of the centrate (or filtrate), elimination of corrosive organic solvents, etc.). The shift of the mother liquor solubility parameters away from water is only slight and can be measured by the standard mixing rules.

From experiments, useful co-solvents include solvents with hydrogen solubility parameters between 4.0 and 26.0 and polar solubility parameters between 3.3 and 13.0. The amount of co-solvent required is a function of its solubility parameter. Particularly preferred solvents, which gave the best results in reducing foam and increasing the speed of isolation, were acetone and cyclohexanol.

The following is a synopsis of a preferred process for purifying a crude phenyl ester salt, Compound (1), via water crystallization with a co-solvent addition. Crude Compound (1), dissolved in deionized water heated to 85° C. and the pH adjusted to about 5 with sulfuric acid to minimize Compound (1) hydrolysis. The solution was agitated at a temperature of 75–85° C. for 1 hour, and then cooled to ~20° C. over 3 to 9 hours. If desired, the solution can be seeded with Compound (1) (previously crystallized from water) at about 14° C. above the solution's crystallization point. Also, during the cooling period, a co-solvent was added when the solution had cooled to a temperature ranging from 40–20° C. Once the solution had cooled to 20° C., the mixture was agitated for an additional hour. The crystallized phenyl ester salt was filtered or centrifuged, washed with either the co-solvent or a co-solvent/water mixture, and then dried in a vacuum oven with a nitrogen purge at 70–100° C. Typically, this affords a phenyl ester salt, such as Compound 1, (80% Compound (1) recovery) as a white crystalline solid with an HPLC assay in the range of 97–100%, and with a color measured as Hunter color L in the range of 89–95.

Advantageously, adding a co-solvent eliminates filtration obstacles encountered in water-only recrystallization processes. The filtration times were decreased and the filtrate foaming was reduced/eliminated. The level of co-solvent may vary from 1% to 50% by weight but is preferably in the range 2% to 20% by weight. The optimal level of co-solvent varies with the solvent type, its effect on the impurity solubility in the mother liquor, and the temperature at which the separation is effected.

The third recrystallization step, the collecting step, involves isolating the purified salt of a phenyl ester from the crystallization liquors. In the same way as discussed above, the recrystallized phenyl ester salt may be collected or isolated from the crystallization liquors using the techniques discussed and any device capable of delivering an efficient separation of solid and liquid phases. Preferably, the recrystallized phenyl ester salt is collected by filtration and optionally dried, again as discussed above.

(F) Dissolving the Collected Phenyl Ester Salt in a Solvent to Form a Solution

Any solvent capable of dissolving the collected phenyl ester salt to form a solution may function as a suitable dissolution solvent. Preferred solvents are relatively inexpensive, non-reactive, non-toxic, non-hazardous, easily volatilized, and do not interfere with the efficiency of the media used for later color removal. Two preferred solvents are acetic acid and water. In the overall process it is preferred to use the same solvents for this step as used for the spray drying step. Preferred solvents for use in this and the spray drying step include polar protic solvents, such as water, methanol, propanol, or isopropanol.

The dissolution step may take place using a heated solvent to dissolve the collected phenyl ester salt. Preferably, the temperature of the solvent is just above the minimum temperature required to completely dissolve the phenyl ester salt. The higher the concentration of the phenyl ester salt in the solvent, the higher the temperature required to keep material in solution. By way of example, typical temperatures used when water is the solvent is 60–80° C.

If water is used as the dissolution solvent the pH is preferably lowered to decrease hydrolysis, and thus loss, of the phenyl ester salt. The preferred pH range is 4–6. Very low pH, less than about 2, may also cause acid hydrolysis of the phenyl ester salt and should be avoided. Any acid may be used to adjust pH. Acids preferred for this purpose include, but are not limited to, sulfuric acid, hydrochloric acid, and acetic acid or mixtures of such acids.

(G) Decolorizing the Solution

Having dissolved the collected phenyl ester salt in a solvent, the process of the invention then decolorizes the solution to remove color bodies from the phenyl ester salt. This decolorization step may be accomplished using a heated solution to maintain the solubility of the phenyl ester salt in the solvent. Decolorization may be accomplished by adsorption of color bodies onto a solid phase adsorbent or by chemical means. Decolorizing a phenyl ester salt may be accomplished using batch methods or column methods. When using the batch method, an amount of adsorbent is added to the phenyl ester salt solution. A column method passes the solution over or through a bed of the adsorbent material.

In one embodiment, the solution is contacted with activated carbon to adsorb color bodies. This step removes color bodies from the solution by contacting the solution with activated carbon (charcoal) for a period of time to promote adsorption of the undesirable color bodies on the surface of the activated carbon. Contacting the solution with activated carbon can be achieved several ways. For example, activated carbon may be simply added to the solution or combined with the phenyl ester salt prior to dissolution. The activated carbon may be removed from the solution by filtration, centrifugation, or other separation techniques known in the art. Alternatively, the solution may be passed over a stationary bed of activated carbon. Carbon beds may be used on an industrial scale but can be labor-intensive and may cause carbon contamination of the phenyl ester salt. Or, the solution may be passed through a filter impregnated with activated carbon (e.g., a Cuno Zeta-Plus filter). Use of an impregnated filter is preferred to adding activated carbon to the solution because a filter does not have the operational difficulties of handling finely divided activated carbon or isolating the activated carbon following treatment. This also avoids isolation of the carbon after it is added to the salt of a phenyl ester solution.

In another embodiment, the solution may be decolorized by contacting it with a resin (a batch method) or by passing it through a resin column (a column method). Suitable resins include, but are not limited to, Dowex Optipore L285 and Dowex Optipore L493 resins, (supplier: The Dow Chemical Company Midland, Mich.); Amberlite IRA 95, Amberlite XAD7, and Duolite A561 resins, (supplier: Rohm and Haas Company, Independence Mall West, Philadelphia, Pa.); Macronet MN100 and Macronet MN200 resins, (Supplier: The Purolite Company, Bala Cynwyd, Pa.); and Diaion PA308 and Diaion HP20 resins, (Supplier: Mitsubishi Chemical America, Inc., White Plains, N.Y.). As with the activated carbon, the resin may simply be added to the solution to adsorb color bodies and then removed by filtration or other known separation techniques. When the solution is decolorized using a resin column, the temperature of the column should be maintained to prevent precipitation of the phenyl ester salt while passing through the column. Flow rate through the column is controlled to insure the proper residence time for color body removal.

When using a resin column to decolorize the phenyl ester salt, it is preferable to regenerate the column for use in subsequent decolorization steps or purification processes. The saturation capacity of the adsorbent bed making up the column determines the length of time that the bed can be online before regeneration. The greater the saturation capacity, the more attractive the process. However, the capacity of the bed may be higher, depending on the quality of the feed. Generally, the darker the feed solution of the phenyl ester salt, the earlier the need for regeneration. The amount of color bodies adsorbed on the bed may be improved by using low temperatures, higher feed concentrations (high percent of solids in the feed), and adjusting the pH range. The color of the phenyl ester salt (lack of color bodies) my also be improved by increasing the residence time and passing the feed through multiple columns.

To decolorize a phenyl ester salt via the column method involves several steps. The decolorization involves most, if not all, of the following steps: 1) a feed step, the period when the column is purifying the feed; 2) a rinse step, when the feed is rinsed off the column with a "feed solvent" or a solvent that is miscible with the feed solvent, (e.g. water or acetic acid); 3) a regeneration step, when the column may be regenerated to prepare it for treating more feed (this may involve more than one step); and 4) a post-rinse, when the column is rinsed with an appropriate solvent to displace the regenerate and to avoid cross-mixing during the subsequent feed step.

One method of regenerating the column treats the resin with an aqueous base, such as an aqueous sodium hydroxide solution (5% concentration). Hydrolysis or ionization of the color bodies, if the treatment increases solubility in the eluent, will then cause desorption of the color bodies. Another method is to treat the resin with an organic solvent, such as methanol, acetone, ethanol, or isopropanol. The color bodies of the resin are highly soluble in organic solvents, often causing the color bodies to desorb. When acetic acid is the solvent, a caustic step or even a water rinse often is sufficient to regenerate the bed. It will most likely be easier to regenerate the resin with water when acetic acid is the solvent. After regeneration, the rinse water should appear colored, indicating that at least partial regeneration was achieved. The rinse causes a pH shift in the resin, which in turn is believed to cause the color bodies to desorb. A further aqueous sodium hydroxide (or other aqueous base solution) treatment followed by methanol (or other organic solvent) may be needed to fully regenerate the column. However, since adsorption occurs from an organic phase, it is unlikely that the organic solvent regeneration step is necessary when the solvent is acetic acid. Rinsing the bed with pure acetic acid creates a concentration driving force favoring desorption.

The resin may also be regenerated when water is used as solvent. To regenerate a saturated bed when the solvent is water, both a base washing step and an organic washing step (as described above) are often needed. Regeneration of water usually achieves greater color removal, however, regeneration will probably need a further base washing step, as described above. Methanol is most often the preferred solvent for the base-washing step, but a decision on which solvent to use should be based on the entire purification section.

Decolorizing the phenyl ester salt may also be accomplished by chemical means, by contacting the solution with a bleaching agent. The bleaching agent can be added directly to the phenyl ester salt solution. Alternatively, solution of the bleaching agent solution can function as a portion of the solvent that is used to dissolve the phenyl ester salt. Any bleaching agent that successfully decolorizes the salt of a phenyl ester without resulting in the decomposition of the salt of a phenyl ester is suitable for the purposes of this invention. Suitable bleaching agents include, for example, hydrogen peroxide, organic peracids (such as peracetic acid), or organic peroxides (such as benzoyl peroxide). A preferred bleaching agent is hydrogen peroxide.

The amount of bleaching agent added to the solution should be sufficient to decolorize the phenyl ester salt. Typically, the amount of bleaching agent added to the phenyl ester salt solution ranges from 0.1 to 10 weight percent. Preferably, the amount of bleaching agent ranges from 0.5 to 5 weight percent. When using the bleaching agent to decolorize a phenyl ester, the bleaching agent should not be so strong or be present in such an excess amount to cause the salt of a phenyl ester to decompose.

Hydrogen peroxide is generally added as an aqueous solution having hydrogen peroxide concentrations ranging from about 3 weight percent to about 30 weight percent. The more concentrated the hydrogen peroxide solution, the smaller the amount needed to remove color bodies from the solution. Generally, when the strength of the hydrogen peroxide is below about 3 weight percent, sufficient decolorization does not occur and when the strength of the hydrogen peroxide is greater than about 30 weight percent, decomposition of the salt of the phenyl ester may result.

(I) Spray Drying the Phenyl Ester Salt Solution to Form a Powder

After decolorization, the phenyl ester salt solution is spray dried to form a powder of the phenyl ester salt. Spray drying the solution may be accomplished using any spray drying techniques and apparatus known in the art capable of the near-instantaneous evaporation of solvent. Spray drying offers the advantage of essentially complete recovery of the non-volatiles from the solution. Thus, the recovery is generally higher than would be obtained from a crystallization/separation/drying process. In addition, the powder obtained from spray drying is generally more amorphous than material isolated through a crystallization process. Amorphous solids generally dissolve at a faster rate than crystalline solids. Advantageously, spray-dried phenyl ester salt powders may have a higher perhydrolysis rate than highly crystalline phenyl ester salts. Spray drying is an attractive alternative to a crystallization/separation/drying process.

As discussed above, the process of the invention spray dries a solution of the phenyl ester salt to produce a phenyl ester salt powder. The solution of the phenyl ester salt may be spray dried using the solution from the decolorization step or the decolorization solvent may be removed, drying the decolorized phenyl ester salt, and the phenyl ester salt redissolved in a solvent for spray drying. Preferred solvents for use in the spray drying step include polar protic solvents, such as water, methanol, propanol, or isopropanol.

The phenyl ester salt is spray-dried using conventional spray-drying techniques and apparatus. Spray-drying is well known in the art, and is described for example, in U.S. Pat. No. 4,424,138, U.S. Pat. No. 4,460,700, and U.S. Pat. No. 4,629,771, which are hereby incorporated in their entirety. Thus, the phenyl ester salt solution is passed through a suitable atomizer, which creates a spray or dispersion of droplets. A stream of a hot gas is arranged to contact the droplets and cause evaporation of the solvent and other liquids present. The solid product separates and is then collected. Suitable atomizers for producing the droplets of the suspension include nozzle atomizers and spinning disc atomizers.

The preferred gaseous medium for effecting the spray-drying is nitrogen having a high degree of purity, but any other gaseous medium which will have no deleterious effect on phenyl ester salts may also be used. Alternative gases include inert gases such as argon or helium.

The hot gas may be arranged to pass in a countercurrent flow to the droplets of the suspension but typically a co-current flow of the hot gas and the suspension is used. Using a co-current flow, the atomizer is typically located at the top of the spray-drying apparatus and the hot gas is introduced into the top of the apparatus and is removed from near the bottom of the apparatus. Some of the spray-dried solid collects at the bottom of the apparatus, from which it may be removed, preferably continuously by suitable means such as a star feeder valve, a screw conveyor, or in the hot gas stream. As is known in the art, the conditions of spray-drying can be adjusted to give any desired particle size.

To prevent the ingress of oxygen-containing materials into the spray-drying apparatus, it is preferred to operate at a slightly elevated pressure, for example at about 1.2 kg/cm$^2$ absolute. The spray drying temperature is generally below the solvent's boiling point (under the pressure conditions existing within the spray-drying apparatus). The temperature should be high enough to cause sufficient evaporation of the solvent to dry at least the outer surface of the droplets before they reach the wall, or discharge point, of the spray-drying apparatus. Preferably, the spray-drying temperature is relatively low and, thereby avoids any deleterious effect on the spray-dried phenyl ester salt. Preferably, the temperature of the hot gas introduced into the spray-drying apparatus does not exceed about 200° C. and the temperature of the droplets, or the spray-dried material, does not exceed 150° C. More preferably the maximum temperature of the droplets, or the spray-dried material ranges between 80° C. and 130° C.

One of ordinary skill would appreciate that in addition to the steps described above, solid materials that occur in the process may be dried if desired using standard techniques and solutions may be filtered or centrifuges to remove unwanted insoluble materials. The aspects of the process of the invention discussed above are illustrated in the following examples. These examples are intended to illustrate, not to limit, the claimed invention.

EXAMPLES

General Methods and Procedures

In the following examples the phenyl ester salt, sodium nonanamidohexanoyloxybenzenesulfonate, is identified defined as Compound (1). The starting Compound (1) used in these examples was typically prepared from the reaction of sodium 4-hydroxybenzenesulfonate, acetic anhydride, and nonanamidohexanoic acid in sulfolane with sodium acetate, imidazole, and/or caustic as catalysts(s). This process is described in U.S. Pat. Nos. 5,414,099 and 5,650,527, which are incorporated in their entirety.

Assay (Purity)

Assay or purity of the materials was determined using liquid chromatography.

Color Measurement

Powder color was measured using a Hunterlab Colorquest II spectrophotometer. The samples are analyzed as dry powders in reflectance mode, using a standard powder cell. Standard reflectance tiles are used prior to each analysis to calibrate the spectrophotometer to ensure consistency and accuracy. Hunter Color is an appearance measurement based on reflectance. It is used to evaluate the quality of material with regard to observable color. These examples use the L, a, and b opponent color scales, where L indicates the lightness of a sample with a value of 100 being white and 0 being black. A sample indicates redness if a is positive and greenness if a is negative. A sample shows yellowness if b is positive and blueness if b is negative. The viewing and lighting conditions are specified, so that in theory, this set of numbers taken together represent objectively what the human eye will see. When testing for the Hunter L color, a Hunter L value of 85 or greater is considered a significant improvement in color. Polymeric adsorbents that demonstrated an average Hunter value of 85 or greater were considered to have significantly improved the color of a salt of a phenyl ester.

Bead Making Procedure

To determine its perhydrolysis rate, the phenyl ester salt was formulated into beads. The beads were typically formulated using a powder or solid phenyl ester salt with a surfactant and a chelating agent. A typical formulation is shown below:

| Bead Formulation | |
|---|---|
| Phenyl ester salt (e.g. Sodium 4-sulfophenyl-6-[(1-oxynonyl)-amino] hexanoate) | 1200 g |
| Surfactant (e.g. 10% LAS, linear alkylbenzene sulfonate, Unger DL-85) | 180 g |
| Chelating Agent (e.g. Sodium citrate dihydrate) | 153 g |
| 8% Deionized water | 102 g |

The dry materials were weighed, charged into a one-gallon sigma blade mixer and dry mixed for 1 minute. While mixing, water was added and mixing was continued for about 17.5 minutes. The wet mix bulk density was determined by measuring weight/volume. The material was extruded using the Luwa DG-L I at 90 rpm (using a 0.7 mm/I mm, 19.7% open area die). The extrusion was rounded for 1 minute at 1,350 rpm in the Luwa QJ-230 Marumerizer, followed by drying for 20 minutes at 115° C. in a Luwa MDB-400 fluid bed.

Measurement of Perhydrolysis Rate

Perhydrolysis rate is the percentage of a phenyl ester salt that has undergone perhydrolysis in a specified period of time and at a specific temperature. For the purposes of these examples, perhydrolysis rate is measured at 5 and 30 minutes intervals at 10° C.

The perhydrolysis rate of a phenyl ester salt is measured by adding a weighed quantity of formulated beads comprising the phenyl ester salt, a reference detergent, and sodium perforate monohydrate to a synthetic hard water solution in a chilled dissolution vessel (Sotax Model AT7, modified with a emersion chiller). The solution is maintained at 10° C. and stirred at 150 rpm.

At a specified time interval, an aliquot of the solution is removed and the peracid in the sample is subsequently reacted with potassium iodide and acetic acid at a specified temperature to liberate the iodine. The iodine in the resulting solution is quickly titrated with standardized sodium thiosulfate, from which perhydrolysis rate is calculated.

Example 1—Solvent Slurry 100.2 g crude Compound (1) (89.4% assay [define assay], Hunter color L value of 76.9) was charged to a 1-L flask containing 300.1 g methanol at ambient temperature. The mixture was stirred for 1 hour at ambient temperature then filtered using a Buchner funnel. The wet cake was washed with 100 mL methanol at ambient temperature then dried to constant weight in a vacuum oven (50° C., ~300 mmHg). 84.5 grams (96.5% assay, 91.0% recovery) of a noticeably lighter powder (Hunter L value of 91.4) was obtained.

Example 2—Solvent Slurry 100.2 g crude Compound (1) (85.9% assay, Hunter color L value of 68.5) was charged to a 1-L flask containing 301.0 g acetic acid at ambient temperature. The mixture was stirred for 1 hour at ambient temperature then filtered using a Buchner funnel. The wet cake was washed with 100 mL, acetic acid at ambient temperature then dried to constant weight in a vacuum oven (70° C., ~300 mmHg). 84.4 grams (95.5% assay, 93.7% recovery) of a noticeably lighter powder (Hunter L value of 84.7) was obtained.

Example 3—Solvent Slurry 100.0 g crude Compound (1) (89.4% assay, Hunter color L value of 76.9) was charged to a 1-L flask containing a mixture of 270 g acetone and 30 g water. The mixture was stirred at 50° C. for 1 hour then filtered using a Buchner funnel. The wet cake was washed with 100 mL acetone at ambient temperature then dried to constant weight in a vacuum oven (50° C., ~300 mmHg). 88.9 g (94.7% assay, 94.1% recovery) of a noticeably lighter powder (Hunter L value of 92.8) was obtained.

Example 4—Solvent Slurry 99.6 g crude Compound (1) (89.4% assay, Hunter color L value of 76.9) was charged to a 1-L flask containing 300.3 g acetonitrile. The mixture was stirred at 50° C. for 1 hour then filtered using a Buchner funnel. The wet cake was washed with 100 mL acetonitrile at ambient temperature then dried to constant weight in a vacuum oven (50° C., ~300 mmHg). 97.8 g (89.9% assay, 98.7% recovery) of powder (Hunter L value of 73.4) was obtained. This extraction solvent did not improve assay or Hunter color.

Example 5—Decolorization: Resin Treatment 30 grams crude Compound (1) was charged to a flask containing 70 grams water. The pH was adjusted to about 4.5 by the addition of six drops of sulfuric acid. To this mixture was charged 20 grams Purolite MN100 resin. The flask was placed in a shaker bath and held at 90° C. for 24 hours. The hot mixture was filtered to remove the resin and the filtrate was dried to constant weight in a vacuum oven (~90° C.). The resulting solid was ground to a fine powder and yielded the following Hunter color analysis: L, 87.06; a, 0.08; b, 4.52.

Example 6—Decolorization: Resin Treatment

Same as Resin Treatment—Example 5 except that no resin was added. The resulting solid was ground to a fine powder and yielded the following Hunter color analysis: L, 74.03; a, 1.53; b, 9.97.

Example 7—Decolorization: Resin Treatment 20 grams crude Compound (1) was charged to a flask containing 80 grams acetic acid. To this mixture was charged 20 grams Rohm and Haas XAD7 resin. The flask was placed in a shaker bath and held at 90° C. for 24 hours. The hot mixture was filtered to remove the resin and the filtrate was dried to constant weight in a vacuum oven (~90° C.). The resulting solid was ground to a fine powder and yielded the following Hunter color analysis: L, 82.37; a, 0.24; b, 7.93.

Example 8—Decolorization: Resin Treatment

Compound (1) to be resin-treated was dissolved in water at 90° C. to make a solution of about 6 liters with a solids content of about 21%. The pH of the solution was adjusted to 4.5 by the addition of acetic acid. The feed solution was pumped through a column packed with approximately 300 mL of Dowex L285 resin. The residence time through the bed was on the order of 30 minutes. Fractions (~500–600 grams) were collected as material exited the column. Fractions 7 and 15 were dried to constant weight in a vacuum oven (~90° C.). The resulting solids were ground to a fine powder and yielded the following Hunter color analyses: Fraction 7—L, 86.87; a, 0.18; b, 3.12 Fraction 15—L, 87.62; a, 0.10; b, 3.56.

Example 9—Spray Drying 1000 g of Compound (1) was dissolved in 2800 g of deionized water at ~75° C. Compound (1) solution was pumped using a metering pump through a transfer line heated to 90° C. at ~50 g/min to an Anhydro model Lab I spray dryer. Nitrogen heated to 132° C. was the drying gas. The Compound (1) solution was atomized with 35 psi nitrogen using a two fluid nozzle spraying counter-current to the drying gas. The exhaust gas temperature was ~75° C. The dried product was separated from the drying gas by a cyclone separator. The dried powder had a residual moisture level of 0.19% and a mean volume particle size of 21.6 microns as measured by a Microtac-X 100 particle analyzer.

The powder was then extruded to produce beads. The spray-dried powder required 11.8% water to process it into beads. The original powder required only 6.2%. Five minute perhydrolysis rate increased from 20% for beads prepared from crystallized Compound (1) to 100% for beads prepared from spray-dried Compound (1). 5091:

Examples 10–12 relate to the purification process of a salt of a phenyl ester using crystallization. Examples 13–22 relate to results when a bleaching agent was added in the optional decolorization step. Examples 23 and 24 and the corresponding charts (Tables 1–6) relate to results when the adsorption process was used in the optional decolorization step.

Example 10—Crystallization

Crude Compound (1)/sulfolane reaction mixture (230.9 grams, 31.3% Compound (1), 60.8% sulfolane) was charged to a 1-L jacketed reaction flask containing a mixture of water (65.0 grams) and methanol (350 grams). To dissolve Compound (1), the contents of the flask were heated until the solvent refluxed (about 72° C.). The contents of the flask were held at this temperature for about 25 minutes. The contents of the flask were then cooled to 25° C. over 3 hours at a rate of 15.7 C/hour. The resulting slurry was filtered using a Buchner funnel and washed the cake with methanol (2×50 grams). The wet cake (115 grams) was dried to constant weight and analyzed. The resulting solid (54.3 grams, 71% Compound (1) recovery) had an assay of 94.5% and contained 5.2% sulfolane.

Example 11—Crystallization

Acetic acid (11,000 lbs.) was charged to approximately 5380 lbs. of crude Compound (1)/sulfolane reaction mixture (39.9% Compound (1) and 50% sulfolane) in a 2000-gallon glass unit at about 130° C. The mixture was held for 1 hour at 85–95° C. to complete dissolution. The resulting solution was passed through a Cuno filter housing containing three Zeta Plus Activated Carbon Cartridges (R-32S type), and into a 2000-gallon glass crystallization unit over 8 hours. The resulting solution was reheated to 85–95° C. A vacuum was applied to distill approximately 5,250 lbs. of acetic acid from the unit. After holding for one hour at 85–95° C., the batch was cooled adiabatically by reducing the pressure in the crystallization unit to 200 mm Hg at a rate of 5 mm Hg per minute. When the temperature reached 90° C. or the pressure reached 200 mm Hg, the pressure ramp was slowed to 0.5 mm Hg per minute with a set point of 0 mm Hg. When the temperature reached 81° C., the pressure ramp was halted and the batch was seeded with 2 quarts of Compound (1) seed crystals to initiate crystallization. The batch was held for 2 hours at the current reactor pressure before resuming the pressure ramp. When the temperature of the crystallization unit reached 60° C., the vacuum was released and cooling was continued using glycol cooling to a batch temperature of 40° C. at a rate of 0.20° C. per minute. When the temperature reached 40° C., the cooling rate was increased to 2° C. per minute (or maximum rate possible) using the cold glycol system. Cooling was continued until the batch temperature reached 15–20° C. The batch was filtered on three Nutsche filters. The wet cake was washed with acetic acid (2×1000 lbs./Nutsche filter) then pulled down under plastic with vacuum until a solids concentration of 70% or greater was obtained. This afforded 1481 lbs. (100% basis, 69% recovery) of a crystalline solid which had an assay of 99.7% and yielded the following Hunter color analysis: L=93.22, a=−0.71, b=3.71.

Example 12—Crystallization

Example 11 was repeated except the solution was not filtered through the Zeta Plus Activated Carbon Cartridges (R-32S type). This afforded 1556 lbs. (100% basis, 74% recovery) of a crystalline solid which had an assay of 102.9% and yielded the following Hunter color analysis: L=90.87, a=−0.73, b=4.36.

Example 13—Decolorization: Bleaching

Centrate (100 mL) from the previously centrifuged Compound (1) was treated with 30% hydrogen peroxide (20 drops) at ambient temperature. No immediate color change was noted. Upon standing overnight, a slight color decrease was noted.

Example 14—Decolorization: Bleaching

Three additions of 30% hydrogen peroxide (20 drops each) at 65° C. to Compound (1) centrate (100 mL) resulted in a centrate color reduction from a Gardner 6 to a Gardner 3.

Example 15—Recrystallization

Water (300 grams) and methanol (800 grams) and 3% hydrogen peroxide (300 grams) were charged to a 5-L jacketed flask. Crude Compound (1) in sulfolane mixture (920 grams, 36.3% Compound (1)) was charged to the flask. The mixture was heated to 75° C. The resulting solution was then cooled to 20° C. over three hours. The mixture was filtered using a Buchner funnel. The wet cake was washed with water (2×400 mL) and then isopropyl alcohol (2×400 mL). The crystallized Compound (1) yielded the following Hunter color: L=93.6, a=2.67, b=1.29.

Example 16—Decolorization: Bleaching

Example 15 was repeated except no hydrogen peroxide was used and 600 grams of water was used. The crystallized Compound (1) yielded the following Hunter color: L=87.0, a=−0.55, b=3.90.

Example 17—Decolorization: Bleaching

Isopropyl alcohol (190 grams) and water (125 grams) were charged to a 1-L jacketed reactor. The solvent mixture was heated to 70° C. Crude Compound (1) (100 grams) was added and dissolved with stirring over 30 minutes. Thirty percent hydrogen peroxide (2.7 grams) was charged and stirred one hour at room temperature. The contents of the reactor were cooled to 12° C. over three hours. The resulting mixture was filtered. The resulting cake was washed with an isopropyl alcohol-water mixture (62 grams, 60:40 isopropanol-water). The cake was then dried to constant weight in a vacuum oven (70° C.). The crystallized Compound (1) yielded the following Hunter color analysis: L=89.4, a=0.21, b=8.52.

Example 18—Decolorization: Bleaching

Example 17 was repeated except 5.4 grams of 30% hydrogen peroxide was added. The crystallized Compound (1) yielded the following Hunter color analysis: L=90.4, a=−0.51, b=7.66.

Example 19—Decolorization: Bleaching

Reagent acetic acid (4100 grams) was charged to a 6-liter vessel with three agitators. The acetic acid in the vessel was heated to 90° C. To this vessel, ~1300 grams of crude Compound (1) was added. The analytical assay showed 84.9% crude Compound (1) and the following Hunter color measurement: L=79.2, a=0.59, b=5.4. This material was dissolved and held at 90° C. for one hour. After one hour, 12 grams of 30 weight percent hydrogen peroxide was added to the vessel. This level of hydrogen peroxide represents approximately 0.3% by weight of the Compound (1) in the vessel. The mixture was cooled to 22° C. at 8° C./hour. The slurry was discharged from the vessel, vacuum filtered, and washed twice with 2000 grams of fresh acetic acid. The cake was then dried overnight in a vacuum oven with $N_2$ purge at ~100° C. The dried cake was ground and sampled for Hunter color. The resulting color was measured as: L=91.1, a=−0.03, and b=3.1. The dried and purified Compound (1) was then used to make beads of standard recipe. The bead color was measured to be: L=83.4, a=0.3, and b=7.6.

Example 20—Decolorization: Bleaching

Example 19 was repeated using the same crude Compound (1) except no peroxide was used. The color of the purified Compound (1) and Compound (1) beads were, respectively: L=88.3, a=0.07, b=2.9; and L=77.9, a=0.71, b=7.9.

Example 21—Decolorization: Bleaching

Reagent acetic acid (3915 grams) was charged to a 6-liter vessel with three agitators. The acetic acid in the vessel was heated to 90° C. To this vessel, 1485 grams of crude Compound (1) was added. The analytical assay showed 89.4% crude Compound (1) and the following Hunter color measurement: L=76.0, a=1.10, b=6.7. This material was dissolved and held at 90° C. for thirty minutes. After thirty minutes, 29.7 grams of 30 weight percent hydrogen peroxide was added to the vessel. This level of hydrogen peroxide represents approximately 0.67% by weight of the Compound (1) in the vessel. The mixture was cooled to 22° C. at 8° C./hour. The slurry was discharged from the vessel, vacuum filtered, and washed two to three times with 2000 grams of fresh acetic acid. The cake was then dried overnight in a vacuum oven with $N_2$ purge at ~100° C. The dried cake was ground and sampled for Hunter color. The resulting color was: L=91.7, a=0.15, b=1.5. The dried and purified Compound (1) was then used to make beads of standard recipe. The bead color was then measured to be: L=84.7, a=0.31, b=6.1.

Example 22—Decolorization: Bleaching

Example 21 was repeated using the same crude Compound (1) and nearly the same charge weights, except no peroxide was used. The purified Compound (1) and Compound (1) beads yielded the following colors, respectively: L=91.3, a=0.06, b=1.3; and L=80.0, a=0.31, b=5.4.

Example 23—Decolorization: Resins

Using the apparatus shown in FIG. 1, resins to be evaluated were selected, with test flasks assigned to each resin (plus an additional test flask for the control). To each flask, 30 g of Compound (1) was added followed by 70 g of water at room temperature. This was followed by the addition of six drops of sulfuric acid to adjust the pH to approximately 4.5. Next, 20 g of resin was added to each flask with the exception of the control flask. The flasks were placed in a shaker bath and run for 24 hours at 85° C. This allowed for approximately 24 hours of contact time. The following resins were used in this Example and Examples 24–27: Dowex Optipore L285 and Dowex Optipore L493 resins, (supplier: The Dow Chemical Company Midland, Mich.); Amberlite IRA 95, Amberlite XAD7, and Duolite A561 resins, (supplier: Rohm and Haas Company, Independence Mall West, Philadelphia, Pa.); Macronet MN100 and Macronet MN200 resins, (Supplier: The Purolite Company, Bala Cynwyd, Pa.); and Diaion PA308 and Diaion HP20 resins, (Supplier: Mitsubishi Chemical America, Inc., White Plains, N.Y.).

Figure 2:
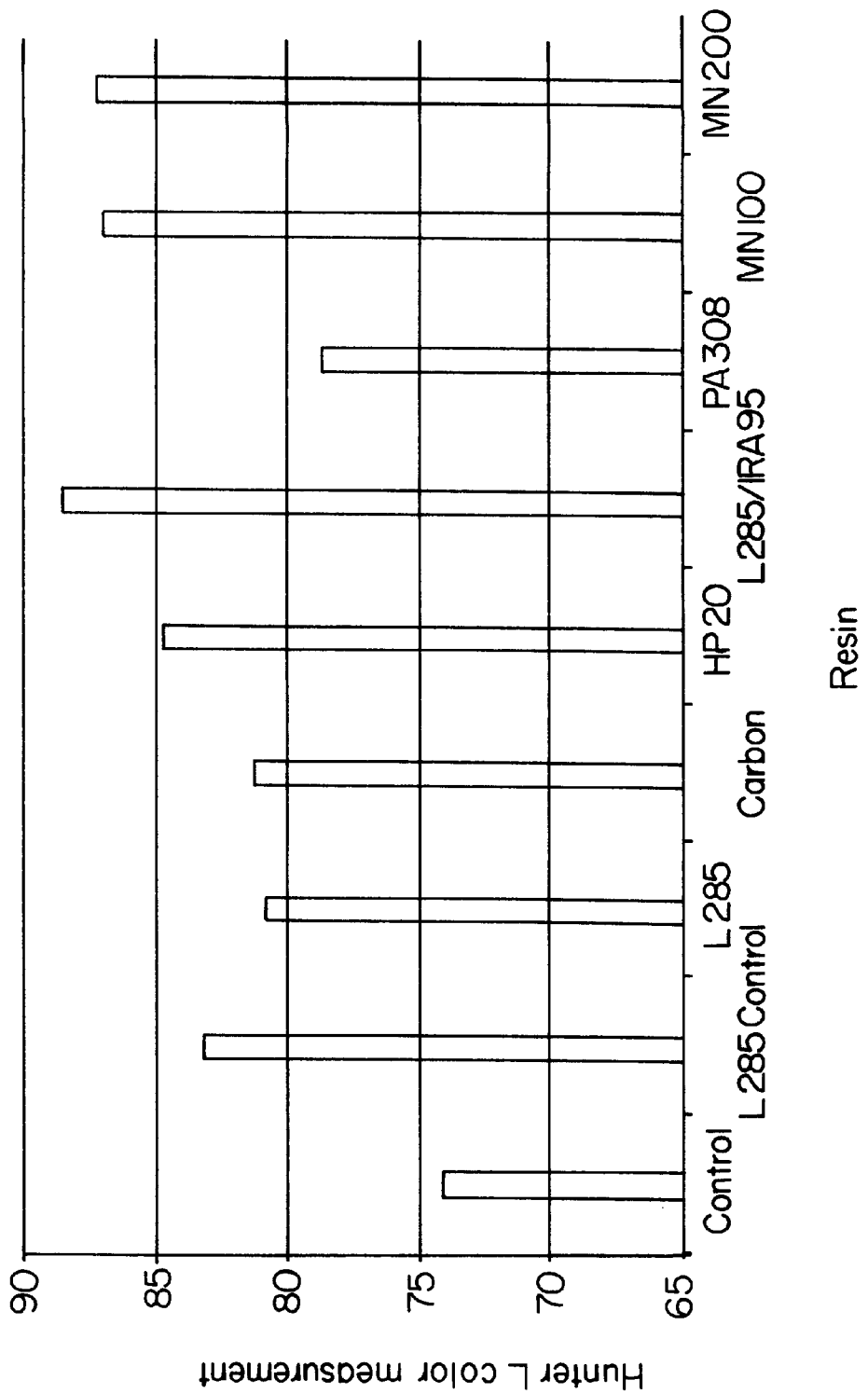
FIGS. 2–4 depict the results from the evaluation of the decolorization resins.

For the Dowex L285 control run, Compound (1) was first heating on a hot plate and dissolved in water. The dissolved Compound (1) was then acidified. Resin was then added to determine the effect of the method acidification and resin addition. After the resin was filtered off, the filtrate was oven dried, powdered, and submitted for Hunter L, a, b measurements. Results of the first batch test are presented in Table 1 and shown in FIG. 2.

All absorbents improved Compound (1) powder color. The combination of Dowex L285 with IRA95 (a weak base resin) gave the best performance. Since IRA 95 is not recommended for use at such high temperatures, it can be replaced by other weak base resins that are stable at higher temperatures.

TABLE 1

Results of the first batch test for the adsorption process

| Run no. | Resin | L | a | b |
|---|---|---|---|---|
| 0 | Control | 74.03 | 1.53 | 9.97 |
| 1 | L285 control | 83.23 | 0.51 | 7.91 |
| 2 | L285 | 80.77 | 0.76 | 8.22 |
| 3 | Carbon | 81.24 | 0.56 | 7.39 |
| 4 | HP20 | 84.78 | 0.38 | 6.28 |
| 5 | L285/IRA95 | 88.46 | 0.01 | 3.64 |
| 6 | PA308 | 78.69 | 0.85 | 8.99 |
| 7 | MN100 | 87.06 | 0.08 | 4.52 |
| 8 | MN200 | 87.39 | 0.19 | 5.30 |

Example 24—Decolorization: Resin

Figure 3:
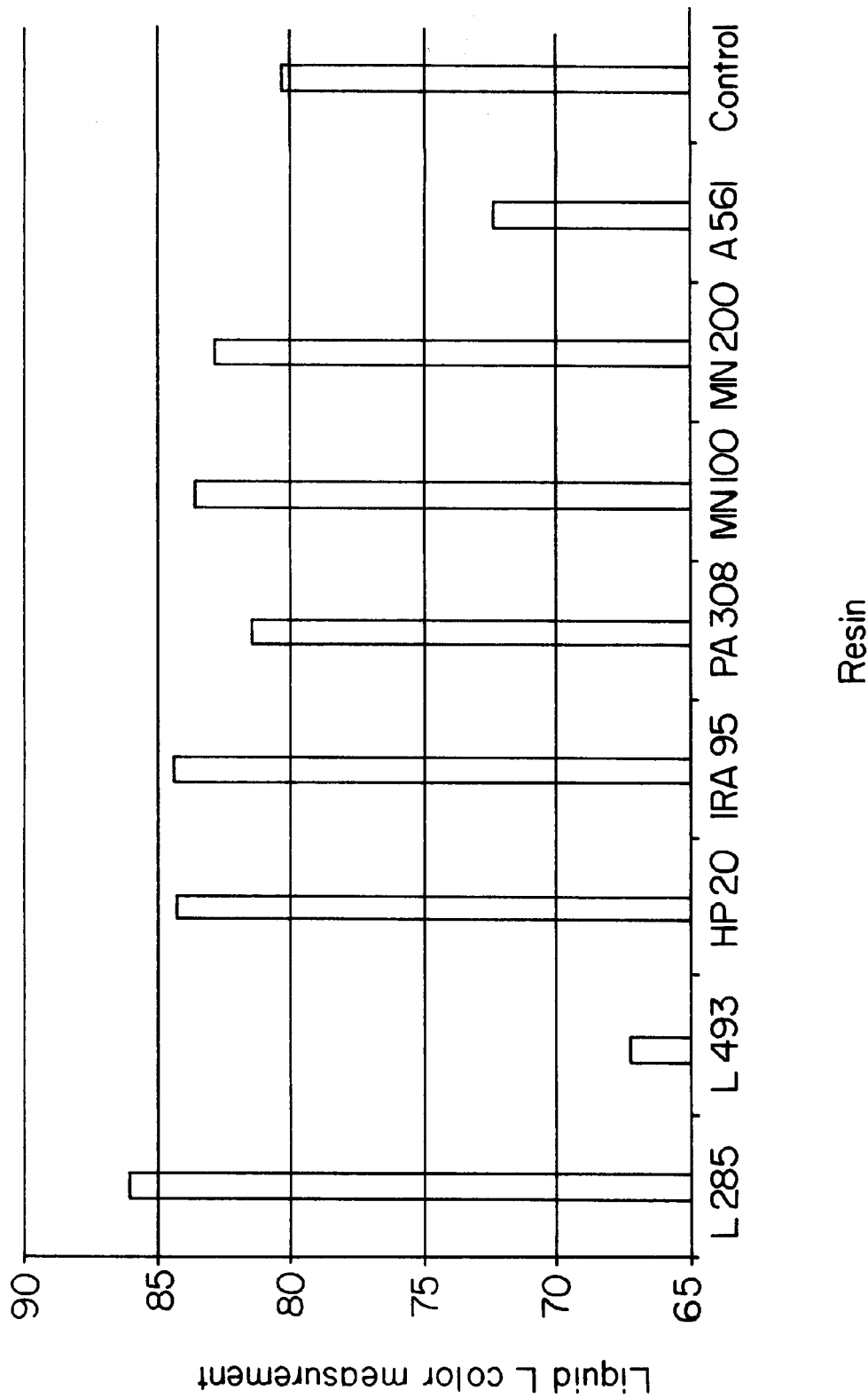

This example was similar to example 23, except for the pH, which was adjusted to 4.0 before the experiment was conducted. Results are presented in Table 2 and FIG. 3. Again, most resins improved Compound (1) color, though L493 and A561 (weak base resin) appear to have done the opposite. Since L493 is very similar to L285 (except that L285 has some weak base functionality and L493 has a higher surface area), the result is probably an experimental error. A561 may have degraded at the high temperature to worsen Compound (1) powder color. Dowex L285 appeared to be the best in this experiment.

TABLE 2

Results of the second batch test for the adsorption process

| Run no. | Resin | L | a | b |
|---|---|---|---|---|
| 1 | L285 | 86.04 | 0.11 | 4.25 |
| 2 | L493 | 67.27 | 1.68 | 11.22 |
| 3 | HP20 | 84.33 | 0.31 | 6.49 |
| 4 | IRA95 | 84.44 | 0.08 | 5.95 |
| 5 | PA 308 | 81.44 | 0.34 | 6.99 |
| 6 | MN 100 | 83.63 | 0.21 | 5.64 |
| 7 | MN 200 | 82.90 | 0.51 | 6.46 |
| 8 | A 561 | 72.47 | 1.75 | 13.16 |
| 9 | Control | 80.39 | 0.61 | 5.54 |

Example 25—Decolorization: Resins

Figure 4:
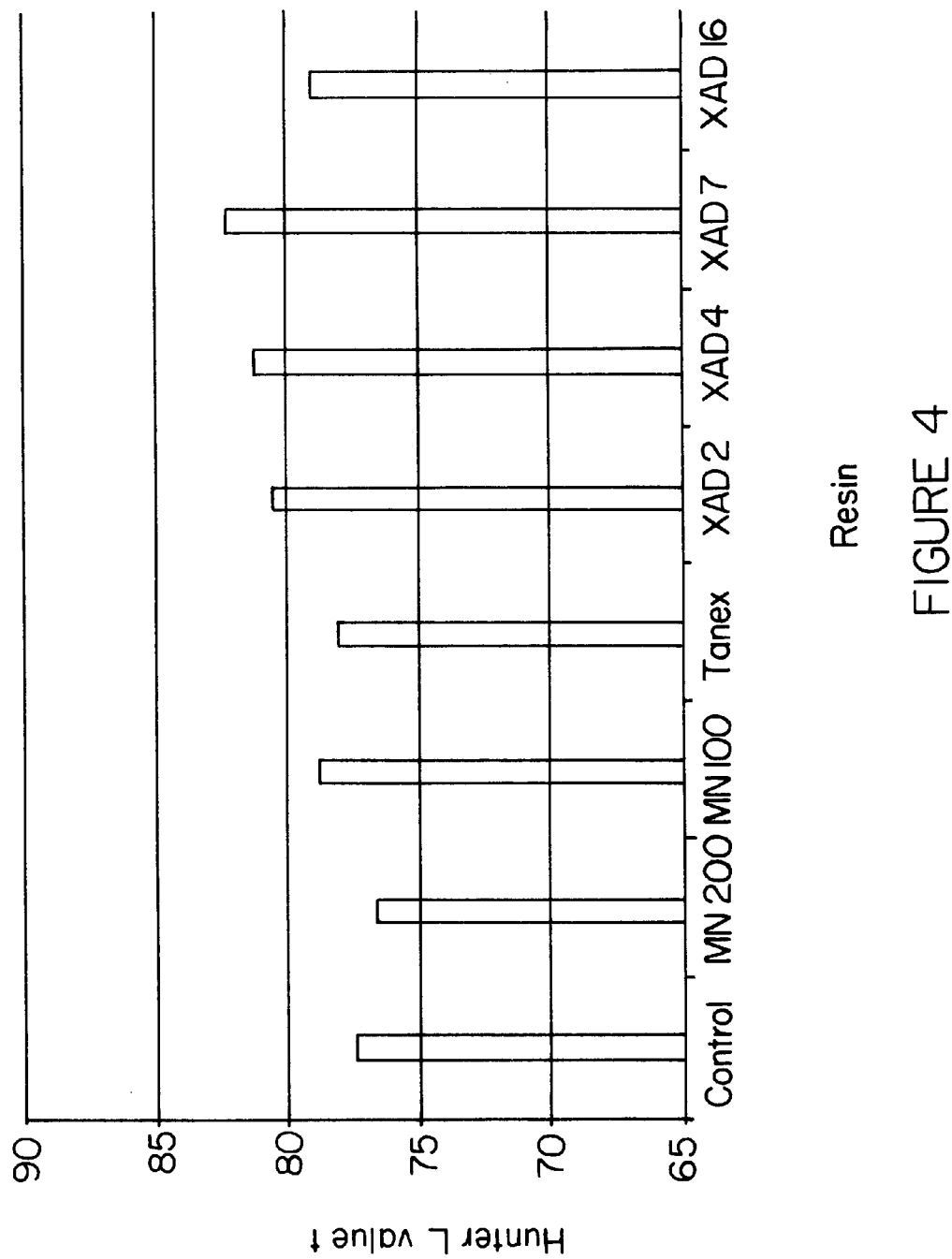

The final batch test experiment was conducted with 20 g of Compound (1) dissolved in 80 g of acetic acid at 85° C. Results are presented in Table 3 and shown in FIG. 4. All resins with the exception of MN 200 showed promise for color removal. XAD7 appeared to be the best from this experiment.

TABLE 3

Results of the third batch test for the adsorption process

| Run no. | Resin | L | a | b |
|---|---|---|---|---|
| 1 | Control | 77.36 | 0.78 | 7.64 |
| 2 | MN200 | 76.59 | 0.81 | 8.46 |
| 3 | MN100 | 78.79 | 0.78 | 5.87 |
| 4 | Tanex | 78.10 | 0.42 | 9.24 |
| 5 | L285 | Not enough sample | | |
| 6 | XAD2 | 80.56 | 0.38 | 7.36 |
| 7 | XAD4 | 81.32 | 0.34 | 7.77 |
| 8 | XAD7 | 82.37 | 0.24 | 7.93 |
| 9 | XAD16 | 79.24 | 0.56 | 7.18 |

Example 26—Decolorization Resin

Initial column tests were conducted with crystallized Compound (1) as feed. The feed was dissolved in acetic acid at about 90° C. to make a solution of 15% solids. The feed solution was pumped through a column packed with approximately 300 mL of adsorbent. Residence time through the adsorbent bed was 30 minutes. Dowex L285 gave the best performance compared to Calgon carbons CPG 12x40 and APA 12x40, Mitsubishi SP207 and SP285, and Purolite MN200. The effectiveness of the resins was judged by visual observation. Many runs were aborted if the performance did not compare favorably with L285. Product from the L285 column was dried overnight in an oven, powdered, and submitted to solid Hunter L, a and b analysis. A fraction consisting of the ninth and tenth bed volume had Hunter L=89.9, which constitutes a substantial improvement (feed: Hunter L=82).

A set of runs were conducted to evaluate color removal by Dowex L285 at a varying pH. The results are presented in table 4. Sulfuric acid was used to lower the pH to 5.4, 4.5, or 4.1. Effluent from the column at pH 4.5 was noticeably lighter than at pH 5.4. However, this is not reflected in the Hunter L results of the fifth fraction from the two runs. The run at pH 4.1 was not noticeably different from the run at pH 4.5. Compound (1) is unstable outside a pH range of 4–6; hence no runs were conducted below pH 4.

To prove the concept of using acetic acid instead of sulfuric acid, a run was conducted (run no. 4) with crude Compound (1) dissolved in water at 90° C. and the pH adjusted to 4.5 with acetic acid. Effluent from the column was comparable to the product of run no. 2. Run no. 4 was similar in all respects to run no. 2, with the exception of the acid that was used to adjust the pH of the solution. Run no. 5 shows that L285 can remove a substantial amount of color from crude Compound (1) dissolved in acetic acid; however, the color removal is lower than when water is the solvent.

TABLE 4

Results of the column tests conducted to evaluate resin performance for the adsorption process

| Run no. | Solvent | Resin | % solids | pH | Acid | Temp. (° C.) | Residence time (min.) | Fraction # | L | a |
|---|---|---|---|---|---|---|---|---|---|---|
| 1 | water | L285 | 17.0 | 5.4 | Sulfuric acid | 90 | 30 | 2 | 88.17 | 0.11 |
|  |  |  |  |  |  |  |  | 5 | 88.39 | 0.08 |
| 2 | water | L285 | 17.5 | 4.5 | Sulfuric acid | 90 | 30 | 5 | 87.93 | 0.47 |
|  |  |  |  |  |  |  |  | 6 | 93.08 | 0.33 |
| 3 | water | L285 | 17.7 | 4.1 | Sulfuric acid | 90 | 30 |  | * | * |
| 4 | water | L285 | 21.1 | 4.5 | Acetic acid | 90 | 30 | 7 | 86.87 | 0.18 |
|  |  |  |  |  |  |  |  | 15 | 87.62 | 0.10 |
| 5 | acetic acid | L285 | 14.3 | — | — | 90 | 30 | 12 | 83.49 | 0.50 |
|  |  |  |  |  |  |  |  | 14 | 82.15 | 0.55 |
| 6 | acetic acid | MN 200 | 21.3 | — | — | 95 | 30 | 6 | 80.85 | 0.81 |
|  |  |  |  |  |  |  |  | 12 | 79.87 | 1.03 |
| 7 | water | MN 200 | 21.0 | 4.5 | Acetic acid | 95 | 30 |  | * | * |

*indicates results not available.

Example 27—Recrystallization
Recrystallization of Crude Compound (1) in Water

A jacketed I-liter flask, equipped with a retreat-curve stirrer and thermocouple, was connected to a computer controlled glycol bath (VWR Model 1169). The flask was charged with deionized water (288 g; ~15.987 mol), crude Compound (1) (100 g, 0.168 mol on an assay basis, 75-36% LC assay), and adjusted to a pH in the range of 5 to 6 with sulfuric acid (0.2 g. 0.02 mol). This slurry was heated to a pot temperature of 85° C. over 30 minutes, at which point the reaction mixture was homogenous. At this time a temperature program was initiated which held the contents at about 80–85° C. (Jacket Temperature 90° C.) for 1 hour before cooling the contents to 25° C. over 3.5 hours. During the cool-down segment, Compound (1) began to crystallize at 61° C.

The slurry was drained from the reaction unit (380 g) and a portion (368 g) was placed in two bottles and centrifuged for 3 minutes at 4000 rpm. The centrate (215.4 g total), which contained 7.12% of the initially charge Compound (1), was removed and replaced with an equal amount of deionized water (216 g total). The samples were slurried and again centrifuged for 3 minutes at 4000 rpm. Again, the centrate (234.3 g total), which contained 3.44% of the initially charged Compound (1), was removed and replaced with deionized water (216 g total). The samples were reslurried and centrifuged for 3 minutes at 4000 rpm. The centrate (223.5 g total), which contained 2.13% of the initially charged Compound (1), was removed providing Compound (1) (126.4 g total) as a water-wet cake. The wet cake was dried in a 70° C. vacuum oven (15 in Hg vacuum) overnight under a nitrogen sweep. This afforded compound 1 (60.5 g; 100.91% LC assay; 82.90% Compound (1) recovery on an assay basis) as a white powder with a color of Hunter L at 93.13, Hunter a at −0.16, and Hunter b at 2.92.

Example 28—Recrystallization
Recrystallization of Crude Compound (1) in Water (Isolation Via Filtration at Higher Temperatures)

Crude Compound (1) (180.3 g, 0.328 mol on an assay basis, 81.8% LC assay) added to deionized water (517.8 g, 28.74 mol) was treated as described in Example 27 without adjusting the pH of the solution. The mixture was cooled to 40° C. over 3 hours, and seeded at 74° C. Compound 1 crystallized at 67° C. The slurry (684.9 g) was filtered at 40° C. on a Buchner funnel, and washed with deionized water (250 g). This afforded Compound (1) (125.1 g; 99.97% LC assay; 69.4% recovery) as a white powder with color of Hunter L at 94.39, Hunter a at −1.01, and Hunter b at 2.0.

Example 29—Recrystallization
Recrystallization of Crude Compound (1) in Water with Acetone as a Co-solvent Crude Compound (1) (125 g, 0.244 mol on an assay basis, 87.67% LC assay) added to deionized water (330 g, 18.318 mol) was treated as described in Example 27 by adjusting the pH to 5.5 after the material had dissolved. During the cool-down segment, the batch was seeded with purified. Compound (1) (1.25 g, 2.8 mmol) at 73° C. The material started to crystallize out of solution at 72° C. Acetone (70 g, 1.205 mol), pre-heated to 40° C., was added to the reaction slurry when the contents had cooled to 40° C. The contents were agitated an additional 1 hour (jacket temperature at 20° C.).

The slurry was drained from the reaction unit (511.9 g) and a portion of the slurry (300 g) was filtered on a course (40–60 microns) glass-sintered funnel (filter area: 44.179 sq. cm) at 253 mm. Hg until the filtrate reached the top of the cake. The filtrate (102.7 g; 105 mL), obtained over 140 seconds, contained 3.28% of the initially charged Compound (1) with a cake height in the funnel at 3.4 cm. A displacement wash composed of a Compound (1)-saturated solution of acetone (128 mL) was added and pulled to the top of the cake. The displacement filtrate (112.2 g; 118 mL), obtained over 214 seconds, contained 5.14% of the initially charged Compound (1) with a cake height in the funnel at 3.5 cm. A reslurry wash composed of a Compound (1)- saturated solution of acetone (170 mL) was added and pulled through the cake. The reslurry filtrate (175.4 g; 208 mL) contained 3.78% of the initially charged Compound (1) with a cake height in the funnel at 3.5 cm. A second reslurry wash using virgin acetone (170 mL) yielded 172 mL (138.3 g) of filtrate, with a cake height in the funnel at 3.5cm. The wet cake (122.9 g) was dried in a 70° C. vacuum oven (15 in Hg) overnight under a nitrogen sweep. This afforded Compound (1) (51.5 g; 98.06% LC assay; 80.56% Compound (1) recovery on an assay basis) as a white crystalline powder with a color of Hunter L at 93.6 1, Hunter a at −0.74, and Hunter b at 2.98.

Example 30—Recrystallization

Recrystallization of Crude Compound (1) in Water with Methyl Isobutyl Ketone (MIBK) as a Co-solvent Deionized water (640 g) was added to a well-agitated 1 liter reactor with baffles. The water was heated to 75° C. Crude Compound (1) (160 g, 89.4% LC assay, Hunter L at 76 ) was added to heated water (640 g, representing 25% crude by weight). After dissolution (30 minutes to 1 hour) the pH was adjusted to 5.5 using $H_2SO_4$. The material was then held 0 to 60 minutes. The solution was cooled from 75° C. to 30° C. at 8 degrees/hour. At approximately 70° C., 2 grams of water-crystallized Compound (1) was added as seed material. Nucleation occurred at 69° C. The material was held at 30° C. from one hour to eight hours. MIBK (5.8 g, 3 wt % of solvent) was added to a 250 gram aliquot of the 30° C. slurry. This mixture was agitated for an additional hour at ambient conditions.

This slurry was filtered on a course (40–60 microns) glass-sintered funnel (Filter area: 50.2 sq. cm) at 253 mm Hg until the filtrate reached the top of the cake. The filtrate (140.3 g; 140 mL), obtained over 209 seconds, contained 3.66% Compound (1) with a cake height in the funnel of 2.9 cm. A displacement wash composed of a Compound (1)-saturated solution of 3% MIBK (60 grams) was added and pulled to the top of the cake. The displacement filtrate (55.1 g; 55 mL) was obtained over 250 seconds. A second displacement wash composed of 100% MIBK (60 g) was added and pulled through the cake. The second wash filtrate collected was 85 g (95 mL) was collected over 409 seconds with a cake height in the funnel of 30 mm. The wet cake (75.6 g, 5.1% Compound (1) was dried in a 90° C. vacuum oven (20 in Hg vacuum) overnight under a nitrogen sweep. This afforded Compound (1) at a 89.5% yield (94.2% LC assay) as a white crystalline powder with a color of Hunter L at 91.2, Hunter a at 0.05, and Hunter b at 1.7.

The claimed invention is:

1. A process for purifying and decolorizing a phenyl ester salt comprising the steps of:
   (a) combining a phenyl ester salt with a solvent to form a mixture, wherein the phenyl ester salt is substantially insoluble in the solvent;
   (b) stirring the mixture for a time sufficient to form a slurry;
   (c) collecting the phenyl ester salt from the slurry;
   (d) optionally drying the collected phenyl ester salt;
   (e) optionally recrystallizing the collected phenyl ester salt;
   (f) dissolving the collected phenyl ester salt in a solvent to form a solution;
   (g) decolorizing the solution; and
   (h) spray drying the solution to form a powder of the phenyl ester salt;
   wherein the phenyl ester salt powder has a higher purity and an improved color as compared to the starting phenyl ester salt.

2. The process of claim 1, wherein the decolorizing step (g) comprises contacting the solution with an adsorbent to remove color bodies.

3. The process of claim 2, wherein the adsorbent is selected from carbon and a resin.

4. The process of claim 1, wherein the decolorizing step (g) comprises contacting the solution with an effective amount of a bleaching agent to remove color bodies.

5. The process according to claim 3, wherein the bleaching agent is hydrogen peroxide which is added as a 3 to 50 percent by weight aqueous solution.

6. The process of claim 1, wherein the process contains a recrystallizing step (e) comprising the steps of:
   combining the collected phenyl ester salt with a recrystallization solvent;
   heating the collected phenyl ester salt and the recrystallization solvent to dissolve the phenyl ester salt and form a recrystallization solution;
   cooling the recrystallization solution to crystallize the phenyl ester salt; and
   collecting the phenyl ester salt.

7. A process according to claim 6, wherein said recrystallization solvent is selected from proprionic acid, acetic acid, methanol/water, and mixtures thereof.

8. A process according to claim 6, wherein step (e) further comprises the steps of:
   washing the phenyl ester salt; and
   drying the phenyl ester salt.

9. A process according to claim 8, wherein the drying step dries the phenyl ester salt in a drying device selected from a ring dryer, a tray dryer, and a rotary-cone vacuum dryer.

10. A process according to claim 1, wherein the optional drying step (d) dries the collected phenyl ester salt in a drying device selected from a ring dryer, a tray dryer, and a rotary-cone vacuum dryer.

11. The process of claim 1, wherein the process contains a recrystallizing step (e) comprising the steps of:
   combining the collected phenyl ester salt with water;
   heating the collected phenyl ester salt and the water to dissolve the phenyl ester salt and form an aqueous solution;
   adjusting the pH of the aqueous solution;
   cooling the aqueous solution to crystallize the phenyl ester salt;
   adding a co-solvent to the aqueous solution; and
   collecting the phenyl ester salt.

12. A process according to claim 11, further comprising the steps of:
   washing the phenyl ester salt; and
   drying the phenyl ester salt.

13. A process according to claim 12, wherein the drying step dries the phenyl ester salt in a drying device selected from a ring dryer, a tray dryer, and a rotary-cone vacuum dryer.

* * * * *